US006319260B1

(12) United States Patent
Yamamoto

(10) Patent No.: US 6,319,260 B1
(45) Date of Patent: Nov. 20, 2001

(54) METHOD OF ENDOSCOPIC MUCOSAL RESECTION USING MUCOPOLYSACCHARIDE AND LOCAL INJECTION PREPARATION

(76) Inventor: Hironori Yamamoto, 2-15-13 Gion, Minamikawachi, Kawachi, Tochigi (JP), 329-0434

( * ) Notice: Subject to any disclaimer, the term of this patent is extended or adjusted under 35 U.S.C. 154(b) by 0 days.

(21) Appl. No.: 09/570,515

(22) Filed: May 16, 2000

(30) Foreign Application Priority Data

Jan. 11, 2000 (JP) .................................................. 12-037240

(51) Int. Cl.[7] .................................................. H61B 17/24
(52) U.S. Cl. .................................................. 606/113
(58) Field of Search .................................. 606/113, 110, 606/37, 46, 79, 148; 600/101, 104, 153, 156; 514/44; 424/93.2; 435/320.1

(56) References Cited

U.S. PATENT DOCUMENTS

| 5,651,788 | * | 7/1997 | Fleischer et al. | ........................ 606/46 |
| 5,998,384 | * | 12/1999 | Shimada et al. | ......................... 514/44 |
| 6,007,546 | * | 12/1999 | Snow et al. | ............................ 606/113 |
| 6,210,416 | * | 4/2001 | Chu et al. | ............................. 606/113 |

OTHER PUBLICATIONS

*Gastroenterology*, 1998 vol. 114, No. 4, G2922:May 20, 1998, DDW at New Orleans (abstract).

Preprint for the 56th Conference of Japan Gastroenterological Endoscopy Society, Nov. 20, 1998, VTR Session (Abstract and English translation).

Preprint for the 57th Conference of Japan Gastroenterological Endoscopy Society, May 11, 1999 Abstract No. 305 (Abstract and English translation).

Preprint for the 57th Conference of Japan Gastroenterological Endoscopy Society, May 11, 1999, Abstract No. 489 (abstract and English translation).

Hirao et al, "Endoscopic resection of early gastric cancer and other tumors with local injection of hypertonic saline–epinephrine", *Gastrointestinal Endoscopy*, vol. 34, No. 3, 1988, pp. 264–269.

"Endoscopic Mucosal Resection for Early Esophageal Cancer by the EEMR–tube (endoscopic esophageal mucosal resection–tube) Method", *Stomach and Intestine*, (Tokyo), vol. 28, No. 2, 1993, pp. 153–159.

* cited by examiner

*Primary Examiner*—Pedro Philogene
(74) *Attorney, Agent, or Firm*—Nixon & Vanderhye

(57) ABSTRACT

Endoscopic mucosal resection is performed by the steps of injecting a local injection preparation containing a biocompatible mucoploysaccharide having no anticoagulant activity, preferably sodium hyaluronate, into the submucosal layer of an affected mucosal tissue to create mucosal elevation, and then, trapping the thus-elevated mucosal tissue with a snare to perform resection. Preferably the local injection preparation further contains a hemostat or angiotonic, and a pharmaceutically acceptable dyestuff.

18 Claims, No Drawings

METHOD OF ENDOSCOPIC MUCOSAL RESECTION USING MUCOPOLYSACCHARIDE AND LOCAL INJECTION PREPARATION

BACKGROUND OF THE INVENTION (1) Field of the Invention

This invention relates to a method of endoscopic mucosal resection. More particularly it relates to a method of endoscopic mucosal resection performed easily and reliably with assistance of a biocompatible mucopolysaccharide having no anticoagulant activity, and to a local injection preparation used therefor.

(2) Description of the Related Art

Endoscopic mucosal resection (hereinafter abbreviated to "EMR") has been widely accepted as a standard procedure for early-stage neoplastic lesions of gastrointestinal tracts. Recently, various modifications of this EMR technique have been introduced. Currently the accepted EMR techniques include a strip-biopsy method or a lift-and-cut EMR, an endoscopic resection after local injection of saline into the submucosal layer, an endoscopic double-snare polypectomy, an EMR using an over-tube, strip-biopsy using two small-diameter endoscopes, an EMR with a cap-fitted panondoscope, and an EMR using a ligation device.

With the improvements in endoscopic resection techniques, good results have been obtained In terms of local cure and long-term outcome after resection. However, these methods still have technical limitations. For example, the strip-biopsy method requires a two-channeled endoscope and it is not suitable for lesions located on the lesser curvature, posterior wall, and cardia of the stomach. With methods using a translucent cap or a ligation device, the size of the resectable mucosa is limited depending upon the size of the device. Further, the endoscopic view is lost by "red-out" while trapping a lesion in these devices. The EMR using an over-tube as well as the strip-biopsy using two-small diameter endoscopes are cumbersome.

In an EMR technique, an affected mucosal tissue is observed with an endoscope and trapped by a snare to perform resection. The affected mucosal tissue does not protrude to a great extent and the surface of mucosa is slippery. Therefore EMR is usually accompanied by technical difficulties, namely, complete removal of the affected mucosa tissue is difficult to attain and complication such as bleeding or perforation sometimes occurs due to unsuccessful operation. To cope with the difficulties, an improved endoscopic resection technique has been proposed wherein endoscopic resection is performed after local injection of normal saline into the submucosal layer of an affected mucosa tissue. However, a problem arises in that the injected saline diffuses quickly with consequent disappearance of the protrusion.

Another proposal has been made wherein hypertonic saline-epinephrine (HSE) or 504 glucose is used as an alternative to the normal saline for preventing or minimizing bleeding during BMR [Hirao M, Masuda K, Asanuma T. Naka H. Noda K, Matsuura K, et al, Endoscopic resection of early gastric cancer and other tumors with local injection of hypertonic saline-epinephrine, Gastroinest Endosc, 1988, 34:264–9; and Makuuch H, Mitomi H, Machimura T, Mizutani S, Shimada H, Sugano K, et al, Endoscopic mucosal resection for early esophageal cancer by the EEMR-tube method, Stomach Intent., 1993;28:153–9]. This proposal still has a problem such that the injected HSE solution or HSE solution containing 50% glucose is emitted from an opening of the mucosa tissue when incised by a needle knife, with consequent disappearance of the protrusion. Further, the hypertonic saline has a histoaffective effect and the problem of complication of bleeding and/or perforation is not solved.

SUMMARY OF THE INVENTION

In view of the foregoing, a primary object of the Invention is to provide a method of EMR performed easily, safely and reliably.

Another object is to provide a local injection preparation used for the method of BM.

In one aspect of the present invention, there is provided a method of endoscopic mucosal resection, which comprises injecting a local injection preparation containing a biocompatible mucopolysaccharide having no anticoagulant activity, preferably sodium hyaluronate, into the submucosal layer of an affected mucosal tissue to create mucosal elevation, and, trapping the thus-elevated mucosal tissue with a snare to perform resection.

In another aspect of the present invention, there is provided a local injection preparation comprising (i) a biocompatible mucopolysaccharide having no anticoagulant activity, preferably sodium hyaluronate, and (ii) a hemostat or angiotonic.

DESCRIPTION OF THE PREFERRED EMBODIMENTS

The EMR technique according to the present invention is characterized as injecting a local injection preparation comprising biocompatible mucopolysacoharide having no anticoagulant activity into the submucosal layer of an affected tissue to create mucosal elevation.

The benefits of the present invention are summarized as follows.

(1) The mucopolysaccharide solution injected into the submucosal layer is not readily diffused, and thus, the elevations made by the injections are steep and remain unchanged for a long time.

(2) Even when the elevated mucosa is partly incised, the injected mucopolysaccharide solution is not readily emitted and the elevated mucosa remains unchanged, and consequently the incision can be safely continued. This benefit is not obtainable with physiological saline, hypertonic saline or 50% glucose.

(3) Although the mucopolysaccharide solution has a high viscosity, its osmotic pressure is not high. Therefore, the mucopolysaccharide solution in not injurious to the tissue and possesses a high safety. EMR can be safely performed even for the colon with a reduced wall thickness. This makes a striking contrast with hypertonic saline or hypertonic saline containing 504 glucose, which Is difficult to use in EMR for the colon because of a considerable risk of perforation.

(4) The mucopolysaccharide solution exhibits a hemostatic affect through mechanical pressure against blood vessels in the submucosal tissue where the solution is injected. Where a hemostat or angiotonic such as epinephrine is incorporated in the mucopolysaccharide solution, the antistatic effect is enhanced to an amazing extent. It is presumed that a hemostat or angiotonic is dissolved in the viscous solution and remains in the injected solution, thus enhancing durability of the hemostat effect. The hemostat effect in safe as contrasted with that manifested by ethanol or hypertonic saline, utilizing tissue injury.

As preferable examples of the mucopolysaccharide having no anticoagulant activity, there can be mentioned hyaluronic acid and phamaceutically acceptable salts of hyaluronic acid, and chondroitin sulfate. The mucopolysaccharide used in the invention broadly includes not only biocompatible mucopolysaccharide having no anticoagulant activity in a narrow sense, but also derivatives thereof such as a crosslinked product of hyaluronic acid or its salt, and a composite of hyaluronic acid or its salt, such as cartilage proteoglycan, and a compound containing a major part of the mucopolysaccharide.

More preferable examples of the mucopolysaccharide are alkali metal salts of hyaluronic acid, such as sodium hyaluronate. Hyaluronic acid is a biocompatible glycosaminoglycan having no anticoagulant activity that is widely found in connective tissues of mammalians. It is a thick substance with high viscosity and a marked ability to retain water. Sodium hyaluronate exhibits a hemostatic effect due to its high viscosity and high adhesion to the tissue an well an a thickening effect. Sodium hyaluronate is neither antigenic nor toxic to human bodies, and is already approved for intrajoint injections for osteoarthritis in Japan. Hyaluronic acid and its salts preferably have an average molecular weight of 20,000 to 4,000,000, and more preferably 600,000 to 1,200,000.

The local injection preparation is an aqueous solution containing sodium hyaluronate at a concentration giving an injection preparation having a viscosity suitable for an endoscopic submucosal injection. The higher the concentration of sodium hyaluronate In the injection preparation or the higher the molecular weight of sodium hyaluronate, the higher the iii viscosity of the injection preparation. When the viscosity of the injection preparation is too high, the endoscopic submucosal injection is difficult to give. In contrast, when the viscosity is too low, the mucosal elevation created by the submucosal injection is insufficient. The concentration of sodium .hyaluronate with an average molecular weight of about 200,000 to 4,000,000, preferably about 600,000 to 1,200,000 in the injection preparation is usually in the range of 0.2 to 1.0% by weight/volume. Most preferably, the concentration thereof is approximately 0.5% by weight/volume.

Preferably a substance exhibiting a hemostatic or angiotonic effect such as epinephrine, norepinephrine or isoproterenol is incorporated in the local injection preparation. By the incorporation of a hemostat or angiotonic in the local injection preparation, bleeding is prevented or further minimized. It is to be noted that sodium hyaluronate does not affect the tissue and exhibits a hemostatic effect due to its high viscosity and high adhesion to the tissue, and, when a hemostat such as epinephrine is incorporated in the sodium hyaluronate-containing preparation, the hemostat remains for a longer time due to the co-presence of sodium hyaluronate, and thus, an enhanced hemostatic effect is manifested.

The amount of the hemostat or angiotonic varies depending upon the particular hemostat or angiotonic and the conditions of the affected tissue, but, the hemostat or angiotonic is usually used at a concentration of 0.001 to 0.1 mg per ml of the sodium hyaluronate-containing injection preparation.

A pharmaceutically acceptable dyestuff is preferably incorporated in the local injection preparation. By the incorporation of the dyestuff in the injection preparation, it can easily be confirmed that the preparation has been injected into the submucosal layer of the affected tissue, and the mucosal elevations created by sodium hyaluronate can be visually observed. Thus, EMR can be more easily, more safely and more reliably performed. The dyestuff is not particularly limited provided that it is pharmaceutically acceptable and, for example, includes indigo dyes such as Indigo Carmine. The amount of the dyestuff is preferably in the range of about 0.002 to 0.5 mg, more preferably 0.01 to 0.1 mg, per ml of the mucopolysaccharide-containing injection preparation.

Dosage of the local injection preparation is in the range of about 0.5 to 2.0 ml per puncture. The total dosage per case is about 5 to 15 ml. If a syringe with a too large volume is used, the injection pressure is small and the injection resistance is large, and therefore, a syringe with a small volume of, for example, about 5 ml, is preferably used.

The therapeutic procedures for excision of, for example. neoplastic legions according to EMR comprises the following steps.

(1) A mucosal neoplastic lesion is observed through an endoscope, and a circular incision line is marked outside the margin of the neoplastic lesion by a needle knife, for example, with application of a high frequency current.

(2) At sites, located preferably on a part, remotely located from the endoscope, of the circular incision line, the sodium hyaluronate-containing injection preparation is injected into the submucosal layer of the neoplastic lesion to create a mucosal elevation at the remotely located part of the circle.

(3) The elevated part of mucosa, remotely located, is incised along the circular line by a needle knife.

(4) The sodium hyaluronate-containing injection preparation is further injected into the submucosal layer at sites on intermediate parts of the circular incision line, located on lateral sides of the neoplastic legion, and then, incision is extended to the intermediate parts of the circular incision line.

(5) The injection preparation is further injected into the submucosal layer at sites located on the remaining part of the circular incision line, i.e., on the nearest side to the endoscope, of the marked circle, and incision is extended to the remaining part of the circular incision line.

(6) The injection preparation or physiological saline is injected into the submucosal layer at the central area surrounded by the marked circular incision line to create a mucosal elevation.

(7) A snare is placed along the cut circular incision line to trap the elevated neoplastic lesion, and the trapped lesion is excited by an electric cautery.

The invention will now be described by the following examples that by no means limit the scope of the invention.

EXAMPLE 1

Local Injection Preparation

To 10 ml of each of 0.2, 0.5 and 1.0 w/v % solutions of sodium hyaluronate ("Artz" supplied by Kaken Phrm. Co., Tokyo, Japan, average molecular weight: approximately 900,000) in physiological saline solution, 0.1 ml of indigo carmine ("Indigo Carmine" supplied by Daiichi Pharm. Co., Japan; concentration: 20 mg/5 ml) and epinephrine ("Bosmin" supplied by Daiichi Pharm. Co., Japan; concentration: 1 mg/1 ml) were dissolved to prepare a local injection preparation.

Test for Mucosal Elevation (1)

Mucosal elevation effects of the local injection preparations were tested on resected porcine stomachs.

Each of the local injection preparations was injected at a dose of 0.5 ml at separate sites into the submucosal layer of the stomach by a disposable syringe with 21-gauge needle. For comparison 0.5 ml of normal physiological saline was similarly injected.

The shape of mucosal elevations made by the injections was observed. Further, the change of the shape with time was observed 0.5, 2. 5. 10 and 30 minutes after the injection. The evaluation was conducted on the steepness of the mucosal elevation and the evaluation results were expressed by the following six ratings.

−: no protrusion is visible
+ −: unclear remaining of protrusion
+: a gently-sloping protrusion with obscure margin
++: in-between "+" and "+++"
+++: a prominent protrusion with a clear margin The test results are shown in Table 1.

TABLE 1

| Time elapsing after injection | 30 sec | 2 min | 5 min | 10 min | 30 min |
|---|---|---|---|---|---|
| Normal saline | ++ | + | + − | − | − |
| 0.2% HA*[1] | +++ | ++ | ++ | + | + |
| 0.5% HA*[1] | +++ | +++ | +++ | +++ | ++ |
| 1.0% HA*[1] | +++ | +++ | +++ | +++ | +++ |

*[1]HA: Sodium hyaluronate

Test for Mucosal Elevation (2)

Mucosal elevation effects of the local injection preparations were tested on dogs.

Each of the local injection preparations was endoscopically injected at separate sites into the submucosal layer of the stomach by a syringe with 21-gauge needle. For comparison, 0.5 ml of normal physiological saline was similarly injected.

The shape of mucosal elevations made by the injections was observed. Further, the change of the shape with time was observed 0.5, 2, 5, 10 and 30 minutes after the injection. The evaluation was conducted on the steepness of the mucosal elevation and the evaluation results were expressed by the above-mentioned six ratings. The test results are shown in Table 2.

TABLE 2

| Time elapsing after injection | 30 sec | 2 min | 5 min | 10 min | 30 min |
|---|---|---|---|---|---|
| Normal saline | ++ | + | + − | − | − |
| 0.2% HA*[1] | +++ | ++ | ++ | + | + |
| 0.5% HA*[1] | +++ | +++ | +++ | +++ | ++ |
| 1.0% HA*[1] *[2] | +++ | +++ | +++ | +++ | +++ |

*[1]HA: Sodium hyaluronate
*[2]1.0% HA solution could be endoscopically injected by the syringe, but the injection was accompanied by difficulty because of extremely high viscosity.

EXAMPLE 2

Endoscopic Mucosal Resection

A 62-year-old woman with no significant past medical history underwent colonoscopy for occasional hematochezia. This revealed a large flat-elevated tumor in the rectum. EMR was performed using a new method that was approved by the Ethical Committee of Jichi Medical School, Tochlgi, Japan. A written informed consent was obtained from the patient.

An aqueous 1.0% sodium hyaluronate solution ("Artz", 1; supplied by Kaken Pharm. Co., Tokyo, Japan) was mixed with the same amount of normal physiological saline to prepare an aqueous solution of 0.5% sodium hyaluronate. A small amount of indigo carmine dye was added to the solution. A 5 ml syringe and a 21-gauge endoscopic injection needle (NM-18L: Olympus Optical Co., Tokyo, Japan) were prepared for the procedure.

Following insertion of the colonoscope (CF 230-I; Olympus Optical Co.), careful observation confirmed the presence of a granular type, flat-elevated lesion located in the anterior wall of the rectum. It measured 40 mm by 30 mm in diameter. The tumor was soft and changed shape with air inflation. The endoscopic findings were indicative of a mucosal tumor without deeper invasion. Endoscopic US (UM-2R 20 MHz; Olympus Optical Co.) showed a hypoechoic granular lesion that was limited to the mucosal layer. No lymph nods involvement was noted. Using a topical spray of indigo carmine dye, the margins of the tumor were clearly delineated. Markings for the incision line were placed 3 to 5 mm outside the margin of the tumor using a needle knife (KD-10Q-1; Olympus Optical Co.) and an electrocautery unit (UES-10; Olympus Optical Co.) set at 2.5 for coagulation current (approximately 20 W).

A circumferential incision of the mucosa, as deep as the muscularis mucosae, was made along the incision line around the tumor. The aqueous 0.53 sodium hyaluronate solution was injected via a 21-gauge needle into the submucosa under the incision line in an amount of 1 to 2 ml per puncture to elevate the incision line. The incision with the needle knife was performed safely and without difficulty, even at the proximal edge of the tumor. The incision was made with an output setting of 3.5 and blend current (approximately 40W). It was started from the proximal side (i.e., distant side remotely located from the endoscope) of the tumor. Then a local injection of the sodium hyaluronate solution was made on the lateral sides to which the incision was extended. Finally the same procedure was repeated for the incision of the distal edge (i.e., nearest edge to the endoscope) of the tumor. When the circumferential incision around the tumor was completed, elevation of the mucosa, with local injections of the sodium hyaluronate solution, formed a bank around the tumor. In total, 19 ml of the sodium hyaluronate solution was used. To elevate the tumor, 8 ml of normal physiological saline was injected into the submucosal layer at the center. A polypectomy snare (SD-GU; Olympus Optical Co.) was then placed along the incision line and tightened, and then, endoscopic resection was performed at a setting of 4.5 and a cutting current of approximately 80 W. The tumor was resected in one piece with only a tiny fragment of mucosa remaining at the distal edge. This fragment was removed with a coagulation-biopsy forceps. The entire procedure required 53 minutes. Although minor bleeding occurred as the circumferential incision was made, it was easily managed by applying coagulation current through the needle knife. No other significant complications were noted, and the patient tolerated the procedure well.

The resected tumor measured 41 mm by 33 mm in diameter. Histological assessment revealed intramucosal carcinoma. The margin of the specimen was free of neoplasm along its circumference except for a short segment at the proximal margin where the tumor reached the edge. In the fragment of mucosa that was separated from the mass, no neoplastic change was found. There was no apparent vascular or lymphatic invasion. Based on these findings, the procedure was considered to be a curative resection.

The benefits of the method of endoscopic mucosal resection (EMR) according to the present invention are summarized as follows.

The affected mucosa is elevated to a sufficient extent by the local injection of-the sodium hyaluronate-containing injection preparation, and the mucosal elevation is maintained for a long time because the sodium hyaluronate-containing injection preparation has high viscosity, high adhesion to the mucosal tissue and good hemostatic effect.

Therefore, the lesion can be easily trapped and completely excised by a polypectomy snare without using a special device or lifting. EMR can be performed easily, safely and reliably. A large and flat lesion having a diameter of about 2 cm or larger can be excised. This is in contrast to the conventional EMR whereby a lesion having a diameter of about 1 cm or smaller can be excised.

Bleeding from the neoplastic lesion and perforation can be prevented or minimized, it is expected that the local injection preparation of the invention is used as a hemostat in an DMR therapy.

The method of the invention is suitable for early diagnosis and therapy of a nonpolypoid early neoplastic lesion of gastrointestinal tracts and other lesions treatable with EMR. It can also be employed for microsurgeries on the body surface.

What is claimed is:

1. A method of endoscopic mucosal resection, which comprises injecting a local injection preparation containing a biocompatible mucopolysaccharide having no anticoagulant activity into the submucosal layer of an affected mucosal tissue to create mucosal elevation, and trapping the thus-elevated mucosal tissue with a snare to perform resection.

2. The method of endoscopic mucosal resection according to claim 1, wherein the biocompatible mucopolysaccharide is selected from the group consisting of hyaluronic acid and pharmaceutically acceptable salts thereof, chondroitin sulfate and cartilage proteoglycan.

3. The method of endoscopic mucosal resection according to claim 1, wherein the biocompatible mucopolysaccharide is sodium hyaluronate.

4. The method of endoscopic mucosal resection according to claim 1, wherein the local injection preparation contains sodium hyaluronate having an average molecular weight of 20,000 to 4,000,000 at a concentration of 0.2 to 1.0% weight/volume.

5. The method of endoscopic mucosal resection according to claim 1, wherein the local injection preparation contains sodium hyaluronate having an average molecular weight of 600,000 to 1,200,000 at a concentration of 0.2 to 1.0% weight/volume.

6. The method of endoscopic mucosal resection according to claim 1, wherein the local injection preparation further contains a hemostat or angiotonic.

7. The method of endoscopic mucosal resection according to claim 6, wherein the hemostat or angiotonic is epinephrine.

8. The method of endoscopic mucosal resection according to claim 7, wherein the local injection preparation is an aqueous sodium hyaluronate solution containing 0.001 to 0.1 mg/ml of epinephrine.

9. The method of endoscopic mucosal resection according to claim 1, wherein the local injection preparation further contains a pharmaceutically acceptable dyestuff.

10. The method of endoscopic mucosal resection according to claim 1, which is a method for excision of a non-polypold early neoplastic lesion of gastrointestinal tract, comprising injecting the biocompatible mucopolysaccharide-containing local injection preparation into the submucosal layer of the neoplastic lesion to create mucosal elevation, followed by trapping the thus-elevated mucosa with a snare to perform resection.

11. A local injection preparation for endoscopic mucosal resection which comprises a biocompatible mucopolysaccharide having no anticoagulant activity, and a hemostat or angiotonic; the amount of the biocompatible mucopolysaccharide being such that the injection preparation has a viscosity suitable for endoscopic submucosal injection.

12. The local injection preparation according to claim 11, wherein the biocompatible mucopolysaccharide is selected from the group consisting of hyaluronic acid and phamaceutically acceptable salts thereof, chondroitin sulfate and cartilage proteoglycan.

13. The local injection preparation according to claim 11, wherein the biocompatible mucopolysaccharide is sodium hyaluronate.

14. The local injection preparation according to claim 11, wherein the local injection preparation contains sodium hyaluronate having an average molecular weight of 20,000 to 4,000,000 at a concentration of 0.2 to 1.0% weight/volume.

15. The local injection preparation according to claim 11, wherein the local injection preparation contains sodium hyaluronate having an average molecular weight of 600,000 to 1,200,000 at a concentration of 0.2 to 1.0% weight/volume.

16. The local injection preparation according to claim 11, wherein the hemostat or angiotonic is epinephrine.

17. The local injection preparation according to claim 16, wherein the local injection preparation in an aqueous sodium hyaluronate solution containing 0.001 to 0.1 mg/ml of epinephrine.

18. The local injection preparation according to claim 11, wherein the local injection preparation further contains a pharmaceutically acceptable dyestuff.

* * * * *

UNITED STATES PATENT AND TRADEMARK OFFICE
CERTIFICATE OF CORRECTION

PATENT NO. : 6,319,260 B1
DATED : November 20, 2001
INVENTOR(S) : Yamamoto

It is certified that error appears in the above-identified patent and that said Letters Patent is hereby corrected as shown below:

Column 1,
Line 26, "panodoscope" should read -- panedoscope --.
Line 28, "In term" should read -- in term --.
Line 56, "504 glucose" should read -- 50% glucose --.
Line 58, "BMR" should read -- EMR --.

Column 2,
Line 8, "Invention" should read -- invention --.
Line 12, "BM" should read -- EMR --.
Line 19, "elevation, and," should read -- elevation; and, --.
Line 54, "504 glucose" should read -- 50% glucose --.
Line 54, "which Is difficult" should read -- which is difficult --.
Line 66, "effect in safe" should read -- effect is safe --.

Column 3,
Line 19, "tissue an well an" should read -- tissue, as well as --.
Line 30, "hyaluronate In" should read -- hyaluronate in --.
Line 32, "the iii viscosity" should read -- the viscosity --.
Line 37, "sodium .hyaluronate" should read -- sodium hyaluronate --.

Column 4,
Line 16, "for example." should read -- for example, --.

Column 5,
Line 4, "For comparison 0.5" should read -- For comparison, 0.5 --.
Line 8, "2. 5." should read -- 2, 5, --.

Column 6,
Line 1, ""Artz," 1;" should read -- "Artz," 1%; --.
Line 18, "nods" should read -- node --.
Line 27, "0.53" should read -- 0.5% --.
Line 46, "-GU;" should read -- 6U; --;

UNITED STATES PATENT AND TRADEMARK OFFICE
CERTIFICATE OF CORRECTION

PATENT NO. : 6,319,260 B1
DATED : November 20, 2001
INVENTOR(S) : Yamamoto

It is certified that error appears in the above-identified patent and that said Letters Patent is hereby corrected as shown below:

Column 7,
Line 5, "of-the" should read -- of the --.
Line 18, "minimized, it is" should read -- minimized. It is --.
Line 20, "DMR" should read -- EMR --.

Column 8,
Line 48, "preparation in" should read -- preparation is --.

Signed and Sealed this

Fourth Day of June, 2002

*Attest:*

JAMES E. ROGAN
*Attesting Officer*    *Director of the United States Patent and Trademark Office*